US00PP12166P2

(12) United States Plant Patent
Heims

(10) Patent No.: US PP12,166 P2
(45) Date of Patent: Oct. 23, 2001

(54) HEUCHERA PLANT NAMED 'VEIL OF PASSION'

(75) Inventor: Dan M. Heims, Portland, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/452,026

(22) Filed: Nov. 30, 1999

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—A Para
(74) *Attorney, Agent, or Firm*—Klarquist Sparkman Campbell Leigh & Whinston LLP

(57) ABSTRACT

A new and distinct hybrid of Heuchera plant characterized by a unique combination of dark, silver-veiled foliage, red flowers, and an extended blooming period.

1 Drawing Sheet

The present invention relates to a new and distinct hybrid of Heuchera, of the family Saxifragaceae, which originated as a cross between an unpatented Heuchera named 'Ruby Veil' (seed parent) and an unpatented, unnamed *Heuchera sanguinea* seedling (pollen parent). Due to the fact that the instant plant and the seed parent plant are the result of crosses between several different Heuchera species, no species designations are given.

This new Heuchera plant is a result of a controlled cross of the aforementioned plants at Terra Nova Nurseries, Inc., in Canby, Oreg. This hybrid was selected from a large selection of seedlings. Seed and pollen parent plants were retained to observe habit and to compare with the instant plant. The new variety has been reproduced only by asexual propagation (division and tissue culture). Each of the progeny exhibits identical characteristics to the original plant.

This plant is characterized by the following:

1. Red flowers.
2. Dark leaves with silver veiling.

Asexual propagation by division and tissue culture as done in Canby, Oreg., shows that the foregoing characteristics and distinctions come true to form and are established and transmitted through succeeding propagations.

BRIEF DESCRIPTION OF THE DRAWING

The drawing shows Heuchera 'Veil of Passion' in June in Canby, Oreg.

DETAILED PLANT DESCRIPTION

The following is a detailed description of the new Heuchera hybrid based on observations of two-year old specimens growing in the field in Canby, Oreg. The color descriptions are all based on The Royal Horticultural Society Colour Chart.

Foliage:
- *Type.*—Simple. Evergreen.
- *Shape.*—Cordate.
- *Length.*—8.5–11.5 cm.
- *Width.*—8.5–11 cm.
- *Petiole length.*—11.5–17.5 cm.
- *Margins.*—Crenate-undulate. Ciliolate.
- *Apex.*—Rounded.
- *Base.*—Cordate.
- *Leaf texture.*—Puberulent.

- *Petiole texture.*—Glabrate.
- *Leaf arrangement.*—Rosette.
- *Venation.*—Reticulate.

Size:
- *Height.*—66 cm (3 years old plant grown in Canby, Oreg.).
- *Width.*—23 cm (3 years old plant grown in Canby, Oreg.).

Flower:
- *Type.*—Perfect. Complete.
- *Shape.*—Campanulate, sepals petaloid
- *Size.*—6 mm from sepal tip to sepal tip and from sepal tip to pedicel.
- *Petal count.*—5, insignificant.
- *Petal size.*—3 mm.
- *Petal shape.*—Lanceolate with a clawed base.
- *Sepal count.*—5 parted.
- *Sepal shape.*—Fused. Calyx is campanulate.
- *Sepal size.*—6 mm long, 7 mm wide.
- *Sepal texture.*—Glandular pubescent.
- *Ovary position.*—Partly inferior.
- *Carpel number.*—2.
- *Stamen number.*—5.
- *Inflorescence type.*—Panicle.
- *Flower number per inflorescence.*—100–200.
- *Peduncle width.*—4 mm tapering to 1 mm.
- *Peduncle texture.*—Puberulent.
- *Blooming height.*—55–60 cm.
- *Bloom period.*—Late May to early October in Canby, Oreg.
- *Fragrance.*—None.

Fruit:
- *Type.*—Two-beaked, ovoid, dehiscent capsule.
- *Fertility.*—Moderate fertility.

Habit: Clumping.

Disease: Mild susceptibility to powdery mildew observed on plants grown in Canby, Oreg.

Hardiness: Cold hardy to USDA Zone 4.

Color characteristics:
- *Foliage.*—Spring/Summer: Upper surface where silver in appearance. —RHS201B Grey Group with a cast of RHS 69D Red-Purple Group. Some leaves are RHS 198C Greyed-Green Group. Upper surface, along veins and margins where it is not silver in appearance.—RHS147C Yellow-Green Group.

Lower surface.—RHS 187B Greyed-Purple Group. Fall: Upper surface.—RHS180A Greyed-Red Group.

*Flower.*—Calyx (closed buds). — RHS 45A Red Group. Calyx (open buds) — RHS 51A Red Group at flower tip. RHS 51C Red Group between flower tip and receptacle Petals. —RHS54C Red Group. Anther. —RHS156A Greyed-White Group. Ovary. —RHS149D Yellow-Green Group.

*Peduncle.*—RHS 183A Greyed-Purple Group.

*Fruit.*—RHS 53B Red Group.

DESCRIPTION OF PARENT PLANTS

The instant plant resulted from a cross between Heuchera 'Ruby Veil' and a *Heuchera sanguinea* seedling. Both parent plants originated in Canby, Oreg. Heuchera 'Ruby Veil' was selected as a parent plant for its silver veiling and velvety ruby-red foliage. The instant plant differs from Heuchera 'Ruby Veil' in having red flowers versus tawny-cream flowers and blooms for a longer period of time. The *Heuchera sanguinea* seedling was selected for its cerise flowers and reblooming habit. The instant plant differs from the *Heuchera sanguinea* seedling in having veiled foliage and is larger in size.

I claim:

1. A new and distinct hybrid of Heuchera plant substantially as shown and described, characterized by a unique combination of dark silver-veiled foliage, red flowers, and an extended blooming period.

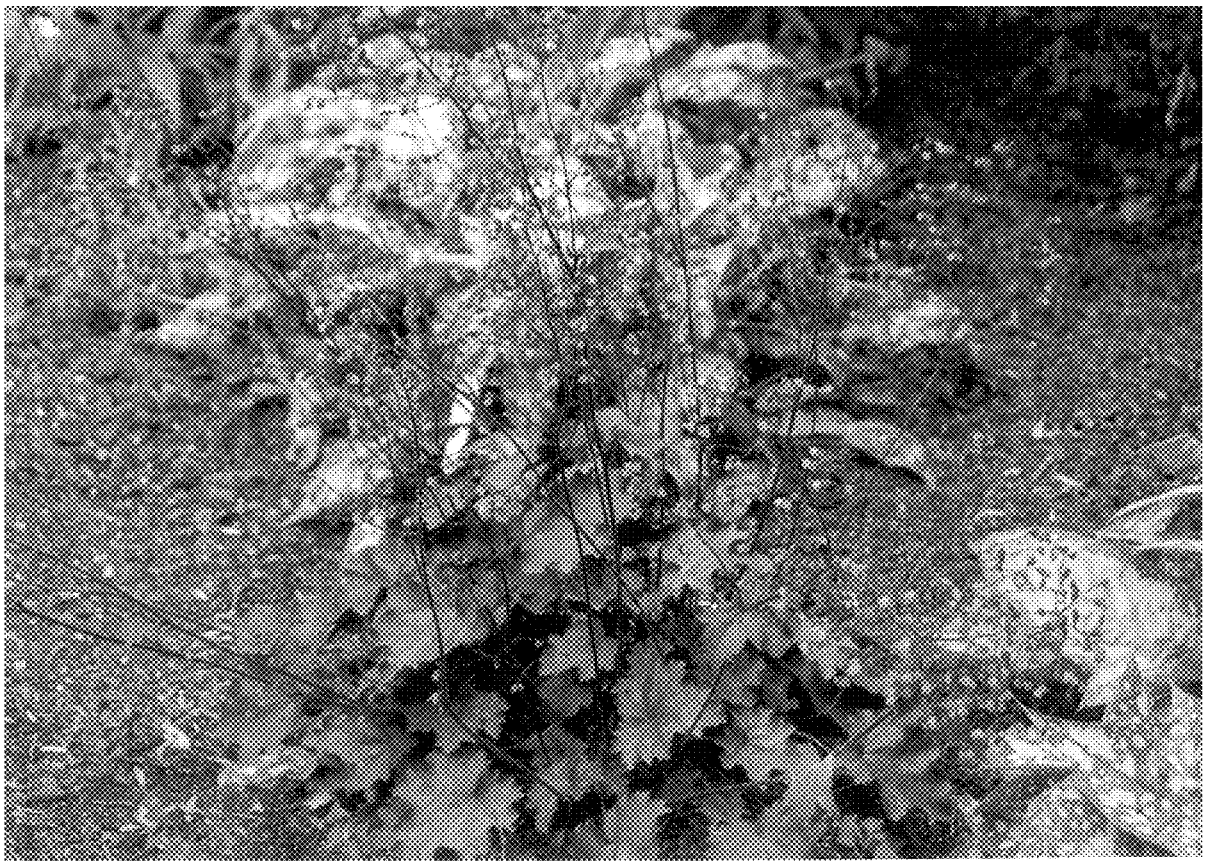

* * * * *